United States Patent [19]

Jentsch

[11] Patent Number: 5,021,182

[45] Date of Patent: Jun. 4, 1991

[54] BACTERIOCIDAL WASHING AGENTS CONTAINING A PER-COMPOUND AND A TAED:PAG MIXTURE

[75] Inventor: Gunter Jentsch, Rodgau, Fed. Rep. of Germany

[73] Assignees: Roman A. Epp; Wolfgang Luderschmidt, both of Fed. Rep. of Germany

[21] Appl. No.: 141,700

[22] Filed: Jan. 7, 1988

Related U.S. Patent Data

[63] Continuation of PCT/DE87/00215, May 9, 1987, abandoned.

[30] Foreign Application Priority Data

May 10, 1986 [DE] Fed. Rep. of Germany ....... 3615788

[51] Int. Cl.[5] .......................... A61L 2/18; C11D 3/39; C11D 3/395; C11D 3/48

[52] U.S. Cl. ...................................... 252/102; 252/95; 252/99; 252/106; 252/186.38; 422/28; 424/660; 424/613

[58] Field of Search ...................... 252/95, 99, 186.38, 252/186.43, 106, 102; 422/28; 424/130; 8/173

[56] References Cited

U.S. PATENT DOCUMENTS 4,663,068 5/1987 Hagemann .......................... 252/99

*Primary Examiner*—Dennis Albrecht
*Assistant Examiner*—Kathlene Markowski
*Attorney, Agent, or Firm*—Omri M. Behr

[57] ABSTRACT

The present invention relates to bacteriocidal washing agents based on surfactants, builders, per-compounds, as well as TAED:PAG mixtures, as well as other adjuvants and additives if necessary which, in particular, allow the bacteriocidal washing and bleaching of laundry at low temperatures.

9 Claims, 3 Drawing Sheets

BACTERIOCIDAL WASHING AGENTS CONTAINING A PER-COMPOUND AND A TAED:PAG MIXTURE

This application is a continuation of International Application PCT/DE87/00215, now abandoned, filed May 9, 1987, which designated the United States.

FIELD OF THE INVENTION

The present invention relates to washing agents based on the surfactants, builders, per-compounds and N,N,N',N'-tetraacetylethylene diamine as acetyl donor as well as other adjuvants and additives, if necessary which, in particular, allow the washing and bleaching of laundry at low temperatures.

PRIOR ART

The significance of per-oxygen bleaching compounds, such as sodium perborate or sodium carbonate, in washing agents for the bleaching of fabrics has been known for a long time. It is also known that to achieve the said bleaching effect of the percompounds, temperatures of above 60° C. are normally necessary. On the other hand it is, however, also known that it is not possible to subject the tissues of synthetic fibers, which are used to an increasing extent, to such high temperatures for the purpose of cleaning them without damaging such tissues.

Thus, during the recent years, considerable efforts have been undertaken to create bleaching systems which are effective at lower washing temperatures, i.e., temperatures of between room temperature and about 60° C., which bleaching systems not only develop their optimum bleaching effect but also allow an effective cleaning at lower temperatures.

The use of per-compounds in the presence of peracid-precursors has been suggested in order to lower the activation temperature. These peracid precursors represent activators for the per-compounds. They form a peracid together with the per-compounds in the washing solution which supplies the oxygen responsible for the bleaching effect.

Suitable activators are N-acyl compounds or O-acyl compounds, in particular N-acetyl compounds or O-acetyl compounds. The N-acyl-and O-acyl compounds (i.e., acyl donors) react with the per-compounds, i.e., the oxygen donors to form percarboxylic acids. N-acetyl compounds and O-acetyl compounds thus yield peracetic acid whose great microbicidal action is known and which is broadly used for chemical sterilization. Examples of such acetyl compounds, suitably acetyl donors are N,N',N', -tetraacetylethylene diamine (hereinbelow named tetraacetylethylene diamine or TAED), pentaacetyl glucose (PAG) and tetraacetyl glycoluril (TAGU).

The in situ formation of peracetic acid has an advantageous effect on the microbicidal efficacy of washing agents which contain these acetyl compounds and per-compounds and which may be employed at low temperatures, i.e., the so-called low-temperature-washing agents. This fact has special significance for hygiene, in particular, hospital hygiene. For hygiene in hospitals, it is extremely important to suppress infections effectively in order to interrupt the transmission paths of infectious diseases. Since, however, in view of the widespread use of fibrous materials, not every item of washing and clothing may be boiled or disinfected at high temperatures, i.e., at temperatures above 90° to 95° C., those additives to washing agents which may be used at low temperatures are advantageous. An example of such a washing agent is the product "Omo with TAED-system", already on the market. Additional examples of such products are those described in GB-A-15 57 568 or in DE-A-28 52 285.

These known washing agents do not exhibit these desired properties to the fullest extent. At lower temperatures, they show only little microbicidal action, deficiencies in the presence of blood and other organic components and/or they have very aggressive properties.

SUMMARY OF THE INVENTION

There is still a demand for washing agents having excellent microbicidal properties which do not have the disadvantages of the known washing agents and which permit washing at low temperatures. The problem underlying the present invention thus resides in providing washing agents, in particular, washing agents suitable for low temperatures which do not have the disadvantages of the known washing agents and which, at lower temperatures, show better microbicidal efficacy than the known washing agents and which moreover, have good storage stability and which are neither aggressive nor corrosive.

Furthermore, these washing agents should be so germicidal that they yield substantially the same "cold sterilizing effect" as peracetic acid.

Surprisingly, it was found that this problem may be solved by the use of mixtures of tetraacetylethylene diamine and specific additional acetyl donors.

DESCRIPTION OF THE PREFERRED EMBODIMENTS

Figure 1:
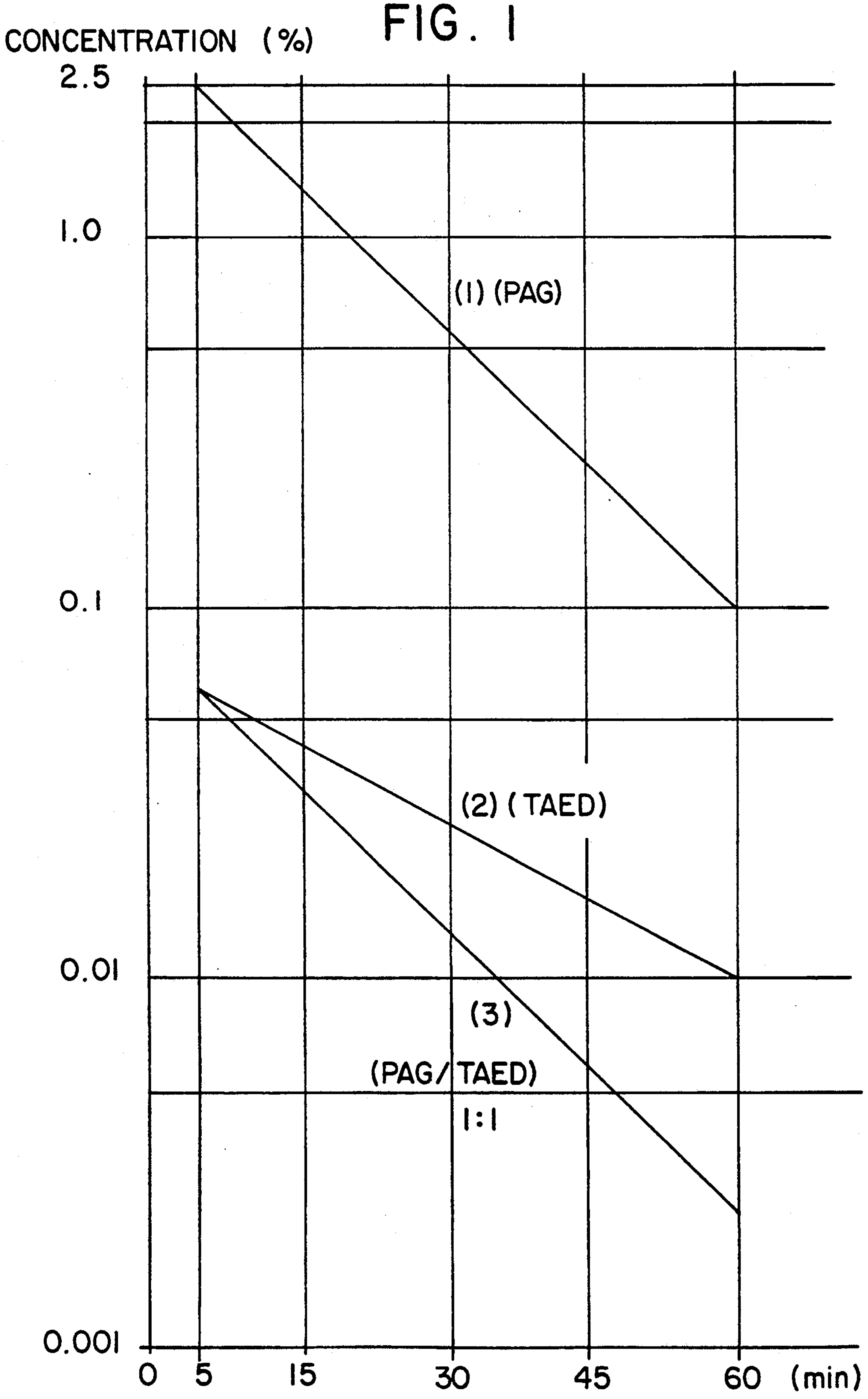

The washing agents according to the present invention, are characterized in that they additionally contain pentaacetyl glucose as further acetyl donor.

The acetyl donor pentaacetyl glucose (PAG) which is useable together with N,N,N',N'-tetraacetylethylene diamine (tetraacetylethylene diamine or TAED) is, like tetraacetylethylene diamine, a known commerical substance. According to the invention, tetraacetylethylene diamine may be mixed with pentaacetyl glucose in the weight ratio of tetraacetylethylene diamine to pentaacetyl glucose, in a ratio of between 0.5 to 1.5 : 1.5 to 0.5, preferably between 0.75 to 1.25 : 1.25 to 0.75 and, most suitably, the weight ratio of tetraacetylethylene diamine to pentaacetyl glucose is 1:1.

Surprisingly, it was found that especially through the novel mixture of tetraacetylethylene diamine and pentaacetyl glucose, the microbicidal effect of washing agents containing such mixtures may be considerably increased at low temperatures whereby, in particular, at a weight ratio of tetraacetylethylene diamine to pentaacetyl glucose of 1:1, a surprisingly synergistic effect is achieved. The latter may be proved on the basis of qualitative suspension experiments.

The mixture of the acetyl donors in the novel washing agent is generally applied in an amount of 2–20% by weight, preferably 4–14% by weight, in particular 6–12% by weight, and for example, in an amount of 6 or 10% by weight.

Suitable as per-compounds or oxygen donors are sodium-or potassium perborate, -percarbonate, -persilicate, -perpyrophosphate, -caroate and/or -percarbamide and/or magnesium monoperoxyphthalate. Preferred, according to the invention, are the sodium salts of the mentioned compounds, especially sodium perborate, -percarbonate, -percaroate, and/or -percarbamide and/or magnesium monoperoxyphthalate. The per-compounds may be used individually or in the form of mixtures of two or more per-compounds. Examples of suitable mixtures are those of sodium perborate and sodium percarbonate, sodium percarbonate and magnesium monoperoxyphthalate, as well as sodium perborate and magnesium monoperoxyphthalate.

The caroate commonly employed is a triple salt of potassium peroxymonosulfate, potassium hydrogen sulfate and potassium sulfate (ca. 45% $KHSO_5$, ca. 25% $KHSO_4$ and ca. 30% $K_2SO_4$).

Magnesium monoperoxyphthalate is preferably used in the commercial form as the hexahydrate. If the magnesium monoperoxyphthalate is not used as the only per-compound, but in admixture with one or several additional per-compound(s), the weight ratios of magnesium monoperoxyphthalate, or magnesium monoperoxy phthalate. $6H_2O$ to the additional per-compounds(s) is 1:1 to 2.5:1, preferably 2:1, and preferably magnesium monoperoxyphthalate, or magnesium monoperoxy phthalate. $6H_2O$ with sodium perborate or sodium percarbonate in the indicated weight ratios are used.

The per-compound may be used in the washing agent of the present invention in an amount of 5–40% by weight, preferably 8–25% by weight and in particular, 10–20% by weight, for example, 15 or 20% by weight.

According to the invention, the mixture of said acetyl donors and the per-compounds are generally used in the ratio of mixture of acetyl donors to per-compounds of 1:0.5 to 10, preferably 1:1 to 3 and in particular of 1:1.4 to 2.1, for example, of 1:1.5 or of 1:2.

The novel mixtures of tetraacetylethylene diamine and pentaacetyl glucose and per-compound(s) may be added to the known common washing agent compositions in the indicated amounts, provided that the additional components of these washing agents are compatible with these mixtures and do not have a disadvantageous influence on the efficiency of the mixtures of of TAED and PAG and per-compound(s) used. Such washing agents generally comprise surfactants, builders and other adjuvants and additives, if necessary.

Examples of suitable surfactants which may be contained in the novel washing agents are preferably anionic and/or nonionic surfactants.

Suitable anionic surfactants are those of the sulfonate, sulfate and carboxylate type, whose molecules comprise at least one hydrophobic hydrocarbon residue and an anionic, cationic, amphoteric, zwitterionic or nonionic group, making it water-soluble. Aliphatic hydrocarbon residues are preferably straight-chained and comprise 10–22, in particular, 12–18 carbon atoms, alkyl-aromatic residues with 8–16, preferably 9–12 carbon atoms in the linear aliphatic residue.

As tensides of the sulfonate type, alkylbenzyl sulfates with $C_9$–$C_{15}$-alkyl groups and the alkane sulfonates, which may be obtained from $C_{12}$–$C_{18}$-alkanes through sulphochlorination or sulphooxidation and subsequent hydrolysis, or neutralization, or through bisulphite addition at olefines, are utilized. An example of such surfactants is sodium dodecyl benzene. Further, suitable surfactants of the sulfonate type are the esters of alpha-sulpho aliphatic acids, e.g., the alpha-sulphonate methyl-or ethyl esters of the hydrated coconut-, palm kernel- or tallow fatty acids, as well as the olefine sulfonates, i.e., mixtures of alkane and hydroxyalkane sulfonates, as well as disulfonates obtained from the mono-olefins with a double bond at the end or within the chain through sulfonation with gaseous sulphur trioxide and subsequent alkaline or acid hydrolysis of the sulfonation products.

Suitable surfactants of the sulfate type are the sulphuric acid monoesters of primary alcohols of natural or synthetic origin, i.e., of aliphatic alcohols, such as e.g., coconut fatty alcohols, tallow fat alcohols, oleyl-, lauryl-, myristyl-, palmityl-, or stearyl alcohol, or the $C_{10}$–$C_{20}$-oxoalcohols and secondary alcohols of this length.

Also the sulphuric acid monoesters of the aliphatic primary alcohols ethoxylated with 1–6 mol. ethylene oxide, ethoxylated secondary alcohols or alkyl phenols are also suitable. Further suited are sulphates, fatty acid alkanolamides and sulphated fatty acid monoglycerides.

As carboxylates, soaps, for example, of coconut or tallow fatty acids and/or of foam suppressing behenacid-containing mixtures may be used.

Furthermore, ether carboxylic acids, such as the salts of carboxymethyl ($C_{10}$–$C_{18}$)-alkyl ethers may be used. An example of such surfactants is soap powder, i.e., a cured tallow soap with portions of sodium arachinate ($C_{12}H_{39}$—COONa) and sodium behenate ($C_{21}H_{43}COONa$).

The anionic surfactants may be provided in the form of their sodium-, potassium-and ammonium salts, as well as, soluble salts of organic bases such as mono-, di-or triethanolamine. Particularly suitable are sodium dodecylbenzyl sulfonate and/or soap powders.

Examples of suitable nonionic surfactants are the addition products of from 2 to 30, preferably 3–15, in particular, 11 mol. ethylene oxide to 1 mol. of an aliphatic compound with substantially 10–22 carbon atoms, of the group consisting of alcohols, alkyl phenols and carbon acids. Among these belong the addition products of 8–30 mol. ethylene oxide to primary alcohols, such as to coconut or tallow fatty alcohols, to oleyl alcohol, to oxoalcohols of the similar chain length or to secondary alcohols as well as to mono- or dialkyl- or alkenyl phenols with 6 to 14 carbon atoms in the alkyl-, or alkenyl residues.

Examples of such compounds are, in particular, the reaction products of straight-chain, saturated $C_{14}$–$C_{18}$-fatty alcohols with 11 mols. ethylene oxide, as well as the reaction products of saturated linear $C_{16}$–$C_{18}$-fatty alcohols with 15–30, in particular, 25 mols. ethylene oxide.

Beside these water-soluble, nonionic surfactants, however, non- or not completely water-soluble polyglycol ethers with 2–7 ethylene glycol ether residues in the molecule are of interest, in particular if they are employed together with water-soluble nonionic or anionic surfactants. Of special practical interest are, due to their good biodegradability; the ethoxylation products of primary aliphatic alcohols and alkenols.

Typical representatives of the nonionic surfactants usable in the invention and having an average ethoxylation degree of 2–7 are the compounds coconut fatty alcohol-3-EO (EO=ethylene oxide), tallow fatty alcohol-5-EO, Oleyl-/Cetyl-alcohol-5-EO, (iodine number 30–50), tallow fatty alcohol-7-EO, synth.-$C_{12}$–$C_{15}$-oxoalcohol-7-EO, i-$C_{15}$–$C_{17}$-alkanediol-5-EO (i=-within the chain); sec.-$C_{11}$–$C_{15}$-alcohol-4-EO.

Exemplary representatives of the nonionic surfactants with an average ethoxylation degree of 8 to 30, in particular, 9 to 15, are the compounds coconut fatty alcohol-12-EO, synth.-$C_{11}$–$C_{15}$-alcohol-9-EO, straight chained saturated $C_{14}$–$C_{22}$-fatty alcohol-11-EO, straight-chained, saturated $C_{16}$–$C_{18}$-fatty alcohol -25-EO.

Furthermore, as nonionic surfactants there may be used the water-soluble addition products of ethylene oxide to polypropylene glycol, alkylene diamine-polypropylene glycol and to alkylpolypropylene glycols with 1 to 10 carbon atoms in the alkyl chain, in which the polypropylene glycol chain functions as a hydrophobic residue. Also nonionic surfactants of the type of the amino oxides or sulphoxides may be used, for example, the compounds N-coconutalkyl-N,N-dimethylaminoxide, N-hexadecyl-N,N-bis(2,3-dihydroxypropyl)-amine oxide, N-tallowalkyl-N,N-dihydroxyethylamine oxide.

According to the present invention, especially preferred nonionic surfactants are the reaction products of straight chain, saturated $C_{14}$–$C_{22}$-fatty alcohols with 11 mols. ethylene oxide and the reaction products of straight-chain saturated $C_6$–$C_{18}$-fatty alcohols with 25 mols. ethylene oxide.

All common inorganic and organic detergent builders which may be used as builders are suitable for use in the mixtures of the invention. Suitable builders are water-soluble salts of phosphates, pyrophosphates, orthophosphates, polyphosphates, phosphonates, carbonates, polyhydroxy sulfonates, polyacetates, carboxylates, polycarboxylates and succinates, as well as zeolites.

Another preferred class of builders are the phosphorus free builders, such as sodium carbonate, sodium bicarbonate, sodium citrate, sodium oxydisuccinate, sodium mellitate, sodium nitrilotriacetate, sodium ethylene diaminetetraacetate and mixtures thereof. Sodium tripolyphosphate is a particularly preferred builder.

In the novel washing agents, the surfactants and builders may be compounded together, generally in the amounts of 10 to 70% by weight, preferably 20–60% by weight, in particular 35–50% by weight.

As further adjuvants and additives, all additives normally used in washing agents may be used in the washing agent as far as the same are compatible with the other components of the novel washing agent and do not impair their effect. Examples of further adjuvants and additives are corrosion inhibitors, greying inhibitors, fillers, complexing agents, optical brighteners, enzymes, perfumes, foam regulators, dyestuffs, neutral salts, antioxidants, hand-improving agents, as well as other adjuvants and additives common in such washing agents.

The mixtures of the invention may comprise one or several corrosion inhibitors.

Suitable corrosion inhibitors are known and common corrosion inhibitors which are compatible with the additional components of the washing agent, such as those for iron, galvanized iron and brass. Examples of suitable corrosion inhibitors are sodium or potassium bicarbonate, -carbonate, -hydrogen phosphate, -dihydrogen phosphate and -pyrophosphate, as well as mixtures thereof and/or sodium disilicate and/or magnesium silicate. In the mixtures according to the invention, sodium disilicate and/or magnesium silicate are preferably used.

The corrosion inhibitor, or the corrosion inhibitor mixture in the novel washing agents is present, preferably in general, in the amounts of 3–15% by weight, preferably 5–11% by weight and, in particular, 6–10% by weight.

The washing agents according to the invention may also comprise greying inhibitors which keep the dirt separated from the fibers suspended in the dye bath and so prevent the greying. Water-soluble colloids, mostly of organic nature, are suited therefor. Examples are the water-soluble salts of polymeric carboxylic acids, glue, gelatine, salts of ether carboxylic acids and/or ether sulphonic acids of the starch or the cellulose or salts of acidic sulphuric acid esters of cellulose or starch. Also, polyamides containing water-soluble acid groups, as well as polyvinyl pyrrolidone, are suited for this purpose. According to the invention, preferably carboxymethylated cellulose, in particular in the form of its sodium salts, is used. Further examples of suitable cellulose ethers are methyl cellulose, hydroxyethyl cellulose, methyl-hydroxyethyl cellulose and methyl-carboxymethyl cellulose, the latter in the form of the sodium salt.

In the washing agents of the invention, the greying inhibitor or mixtures of same, may generally be present in the amounts of 0.5–2% by weight, preferably in amounts of 0.7–1.2% by weight and in particular, in an amount of 1% by weight.

As fillers, the washing agents of the invention may comprise those commonly used in washing agents, provided that they are compatible with the other components Such fillers are sulphates and/or carbonates of the alkali metals, in particular, of sodium and potassium, such as sodium sulphate and sodium carbonate. Such fillers may be utilized in the mixtures of the invention in amounts of 8–50% by weight, preferably 13–26% by weight and in particular, in amounts of 15–22% by weight.

Among the complex formers, which may be contained in the novel washing agents of the invention, are all complex formers commonly used in washing agents, which are compatible with the other components. Examples of such complex formers are ethylenediaminotetraacetic acid, or its homologs or aminoalkanepolyphosphonium acids or hydroxyalkanepolyphosphonium acids, such as 1-aminoethane-1,1-diphosphonium acid, aminotrimethylentriphosphonium acid, 1-hydroxyethane-1,1-diphosphonium acid, as well as their homologs, whereby these compounds are used in the form of their sodium- or potassium salts. According to the invention, ethylene diaminotetraacetic acid disodium is particularly preferred.

The novel washing agents may, in general, contain these complex formers in amounts of 0.1–2% by weight, preferably in amounts of 0.2–1% by weight and, in particular, in an amount of 0.2–0.6% by weight.

The novel washing agents may comprise all optical brighteners commonly contained in washing agents which are compatible with the other components of the washing agent. Examples of such brighteners are the derivatives of the diaminostilbenesulphonic acids, or their alkali metal salts. Suitable are salts of 4,4'-bis(2-anilino-4-morpholino-1,3,5-triazine-6-yl-amino)-stilbene-2,2'-disulphonic acid or analogous compounds, which instead of the morpholino group, carry a diethanolamino group, a methylamino group, or a 2-methoxyethylamino group or which carry a methoxyanilino group, such as disodium-4,4'-bis[4-(p-methoxyanilino)-6-morpholino-1,3,5-triazinyl-2-amino]-stilbene-2,2'-disulfonate. Furthermore, those optical brighteners of the 1,3-diaryl-2-pyrazoline type may be considered, for example, 1-(p-sulphamoylphenyl)-3-(p-chlorophenyl)-2-pyrazoline, as well as similar compounds which carry, instead of the sulphamoyl group, the methoxycarbonyl-, 2-methoxyethoxycarbonyl-, the acetyl amino or the vinylsulphonyl group. Further utilizable are the substituted aminocoumarins, e.g., the 4-methyl-7-dimethyl-amino-or 4-methyl-7-diethylaminocoumarine, 1-(2-benzimidazolyl)-2-(1-hydroxyethyl-2-benzimidazolyl)-ethylene and 1-ethyl-3-phenyl-7-diethylamino-carbostyryl, as well as 2,5-di-(2-benzoxazolyl)-thiophene, 2-(2-benzoxazolyl)-naphto [2,3-b]-thiophene and 1,2-di-(5-methyl-2-benzoxazolyl)-ethylene, as weel as brighteners of the substituted 4,4'-distyryldiphenyl type, e.g., 4,4'-bis(4-chlor-3-sulphostyryl)-diphenyl. The novel washing agents may also contain mixtures of the above-mentioned brighteners. These mixtures preferably comprise optical brighteners in the form of derivatives of the diaminostilbene-disulphone acid, or their alkali metal salts, with di-sodium-4,4'-bis-[4-(p-methoxyanilino)-6-morpholino-1,3,5-triazinyl-(2)-amino]-stilbene-2,2'-disulphonate being particularly preferred.

In the novel washing agents, the optical brighteners may be used in amounts of 0.1–1% by weight, preferably in amounts of 0.1–0.6% by weight and in particular, in an amount of 0.2–0.5% by weight.

Among the enzymes which may be utilized in the novel washing agents are all enzymes which are commonly present in washing agents which are compatible with the rest of the components of the novel washing agents. Suitable enzymes are proteases, amylases and lipases, proteolytic enzymes being particularly preferred. The production of these proteases is effected by extracellular formation of enzymes of microorganisms of the species Bacillus subtilis, or Bacillus licheniformis (cf. Waschmittelchemie, Henkel & Cie., Huthig Verlag, Heidelberg, 1976, pages 162–167).

The novel mixtures may comprises enzymes in amounts of 0.2–1.5% by weight, preferably in amounts of 0.3–1% by weight and in particular, in an amount of 0.3–0.6% by weight.

All perfume oils commonly usable for this purpose are suited, as long as they do not disadvantageously influence the efficay of the novel washing agents.

Examples of suitable perfumes are Cleany (Dragoco) and Citrone (Naarden).

The amount of perfume oil which may be used in the novel washing agents is not critical. In general, 0.2–2% by weight, preferably 0.3–0.5% by weight and in particular, 0.5% by weight perfume oil may be contained in the novel washing agents.

The novel washing agents may, if necessary, also contain dyestuffs, whereby all dyestuffs commonly usable for washing agents are suitable, as long as they are compatible with the other components of the novel washing agent. Examples of suitable dyestuffs are acid red and carmine.

As foam inhibitors in the novel mixtures, all commonly used foam inhibitors compatible with the common components of the novel washing agents may be used. Suited therefor are silicone defoamers and microcrystalline waxes having a melting point within the range of about 35° C. to 115° C. and a saponification value of less than 100, $C_{16}$-$C_{22}$-fatty acids.

If necessary, the novel washing agents may also comprise stabilizers for the bleaching agents or the optical brighteners. All compounds commonly usable for this purpose are suitable therefor, as far as they are compatible with the other components of the washing agent. Magnesium salts, in particular magnesium silicate, are suitable.

The washing agents according to the present invention may have the following composition:

| | | |
|---|---|---|
| (a) | mixture of tetraacetylethylene diamine and pentaacetyl glucose, preferably in the ratio 1:1 | 2–20% by weight |
| (b) | one or more per-compounds | 5–40% by weight |
| (c) | surfactants and builders | 10–70% by weight |
| (d) | one or more corrosion inhibitors | 3–15% by weight |
| (e) | one or more fillers | 8–40% by weight |
| (f) | greying inhibitors | 0.5–2% by weight |
| (g) | complex formers | 0.1–2% by weight |
| (h) | optical brighteners | 0.1–1% by weight |
| (i) | enzymes, preferably proteolytic enzymes | 0–1.5% by weight |
| (j) | perfume | 0–2% by weight |
| as well as water balance, if necessary, | | |
| Particularly suitable are washing agents of the following composition: | | |
| (a) | mixture of tetraacetylethylene diamine and pentaacetyl glucose, preferably in the ratio 1:1 | 4–14% by weight |
| (b) | one or more per-compounds | 8–25% by weight |
| (c) | surfactants and builders | 20–60% by weight |
| (d) | one or more corrosion inhibitors | 5–11% by weight |
| (e) | one or more fillers | 13–16% by weight |
| (f) | greying inhibitors | 0.7–1.2% by weight |
| (g) | complex formers | 0.2–1% by weight |
| (h) | optical brighteners | 0.1–0.6% by weight |
| (i) | enzymes, preferably proteolytic enzyme | 0.1–0.6% by weight |
| (j) | perfume | 0–0.5% by weight |
| as well as water balance, if necessary | | |
| Particularly suitable are washing agents having the following composition: | | |
| (a) | mixture of tetraacetylethylene diamine and pentaacetyl glucose in the ratio of 1:1 | 6–12% by weight |
| (b) | one or more per-compounds | 10–20% by weight |
| (c) | surfactants and builders | 35–50% by weight |
| (d) | one or more corrosion inhibitors | 6–10% by weight |
| (e) | one or more fillers | 15–22% by weight |
| (f) | greying inhibitors | 1% by weight |
| (g) | complex formers | 0.2–0.6% by weight |
| (h) | optical brighteners | 0.2–0.5% by weight |
| (i) | enzymes, preferably proteolytic enzymes | 0.5% by weight |
| (j) | perfume | 0.5% by weight |
| as well as water balance, if necessary | | |

The production of the novel washing agents may be effected in the usual manner, e.g., the washing agents may be produced simply by mixing the components in the indicated amounts in a powder mixer as well as, if necessary, by subsequent granulation. It is also possible to produce the washing agents by mixing several components in so-called premixtures, preferably with simultaneous granulation, and then mixing these premixtures with each other or with additional individual components. A further variant consists in producing an aqueous paste-like mass of the individual components and then subsequently subjecting said mass to spray drying.

The novel washing agents are generally provided in solid form, e.g., as powder or as granulate and used either with water, or added to the dye liquor. Suitable application concentrations depend on the purpose of use. Suitably, 0.25–2.5%, preferably 0.5–2% and in particular, 0.5–1% are used.

The novel washing agents are especially employed for the washing and simultaneous disinfection of laundry, in particular at low temperatures. The use of the novel low-temperature washing agents for cleaning laundry, especially those made of synthetic fibers, has significant importance in the hospital and medical sectors. The novel washing agents have been examined with respect to their disinfecting effect, according to the rules for the examination and evaluation of chemical disinfection procedures (status of Feb. 1, 1984) of the Deutsche Gesellschaft fur Hygiene und Mikrobiologie (DGHM) (German Society for Hygiene and Microbiology). The novel washing agents were found to be excellent agents for washing and disinfecting laundry of the foregoing material. Beside excellent cleansing properties, they show very good microbicidal effects, i.e., they are excellently bacteriostatic, fungistatic, as well as bactericidal and fungicidal and also viricidal. Furthermore, it has been found that these washing agents are not toxic, not aggressive and not corrosive. It is possible to use these washing agents in low concentrations and to subject the laundry to shorter durations of influence at lower temperatures.

The following examples illustrate the additional aspects of the present invention:

EXAMPLES 1-14

Washing agents were produced by using the components shown in Table 1 below. "Tinopol", sold by Ciba Geigy, was used as optical brightener (disodium-4-4'-bis-4-(p-methoxyanilino)-6-morpholine-1,3,5-triazinyl-(2)-aminostilbene-2-2'disulphonate).

Genopol T110, is a polyglycol ether product of general formula $$R—CH_2O(CH_2—CH_2O)_nH,$$

wherein n is 11, which was obtained by reaction of staight-chain saturated $C_{14}$-bis $C_{42}$-fatty alcohols with 11 mols. ethylene oxide.

The product is wax-like, nearly white and of smooth consistency. It comprises the following physical characteristics:

| | |
|---|---|
| Solubility in water (10 g/l): | clear |

-continued

| | |
|---|---|
| density at 50° C. g/cm³: | 0.98 |
| index of refraction at 50° C.: | 1.451 |
| dripping point-°C.: | ca: 40 |
| point of turbidity-°C. in water: | 87–89 |
| iodine color number: | ca: |

As perfume, a product with the name "Cleany", or a common lemon perfume, was used.

TABLE I (Indications by % by weight)

| Examples | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| TAED/PA (1:1) | 10 | 6 | 10 | 10 | 10 | 10 | 10 | 10 | 10 | 10 | 10 | 10 | 10 | 10 |
| Sodium perborate | 15 | 10 | 10 | | | 5 | 15 | 10 | 7.5 | | | 20 | 10 | |
| Sodium percarbonate | | | 5 | 5 | | | | 5 | | | | | | |
| Magnesium-mono peroxyphthalate | | | | 10 | 10 | 10 | | 7.5 | 15 | 10 | | 10 | 20 | |
| Sodium dodecyl benzyl sulphonate | 16 | 12 | 12 | 12 | 12 | 12 | 8 | 8 | 8 | 8 | 8 | 10 | 10 | 10 |
| Genapol T 110 | | 3 | 3 | 3 | 3 | 3 | 4 | 4 | 4 | 4 | 4 | | | |
| Surfactants; wash-active subst. | | | | | | | 3 | 3 | 3 | 3 | 3 | | | |
| Sodium tripoly phosphate | 30 | 36 | 30 | 30 | 30 | 30 | 30 | 30 | 30 | 30 | 30 | 30 | 30 | 30 |
| Sodium metasilicate. $5H_2O$ | 6 | 4 | 4 | 4 | 4 | 4 | 6 | 6 | 6 | 6 | 6 | 7 | 7 | 7 |
| Magnesium silicate | 3 | 3 | 3 | 3 | 3 | 3 | 3 | 3 | 3 | 3 | 3 | 1 | 1 | 1 |
| Sodium sulphate | 15 | 18 | 15 | 15 | 15 | 15 | 15 | 15 | 15 | 15 | 15 | 17.1 | 17.1 | 17.1 |
| Sodium carbonate | | | | | | | | | | | | 3 | 3 | 3 |
| Carboxymethyl cellulose | 1 | 1 | 1 | 1 | 1 | 1 | 1 | 1 | 1 | 1 | 1 | 1 | 1 | 1 |
| Ethylenediamine tetracetic | 0.5 | 0.5 | 0.5 | 0.5 | 0.5 | 0.5 | | | | | | | | |
| Acid, res. 2 Na-salts thereof | | | | | | | | | | | | 0.2 | 0.2 | 0.2 |
| Optical brighteners | 0.4 | 0.3 | 0.3 | 0.3 | 0.3 | 0.3 | 0.4 | 0.4 | 0.4 | 0.4 | 0.4 | 0.2 | 0.2 | 0.2 |
| Proteolytic enzyme | | | | | | | | | | | | 0.2 | 0.5 | 0.5 |
| Perfume | 0.5 | 0.5 | 0.5 | 0.5 | 0.5 | 0.5 | 0.5 | 0.5 | 0.5 | 0.5 | 0.5 | | | |
| Water Ad. | 100 | 100 | 100 | 100 | 100 | 100 | 100 | 100 | 100 | 100 | 100 | | | |

All washing agents showed excellent washing-and cleansing properties during the test.

The washing agent produced according to Example 12 which comprises a proteolytic enzyme for washing agents, produced by the company Rohm, Darmstadt, was subjected to the qualitative suspension test. The qualitative suspension test was conducted according to the rules of the Deutsche Gesellschaft fur Hygiene und Microbiologie (status Feb. 1, 1984), published in Hygiene+Medizin 9 (1984, pages 41-46)m mhp-Verlag, Wiesbaden). The following test germs were used:

*E. coli* (ATCC 11229)

*Staph. aureaus* (ATCC 6538)

*Candida albicans* (ATCC 10231)

As inactivation substance to remove residual peroxides and activators, a mixture of 3% Tween 80, 0.5% sodium thiosulphate, 0.1% histidine and 0.3% lecithin was used.

Figure 2:
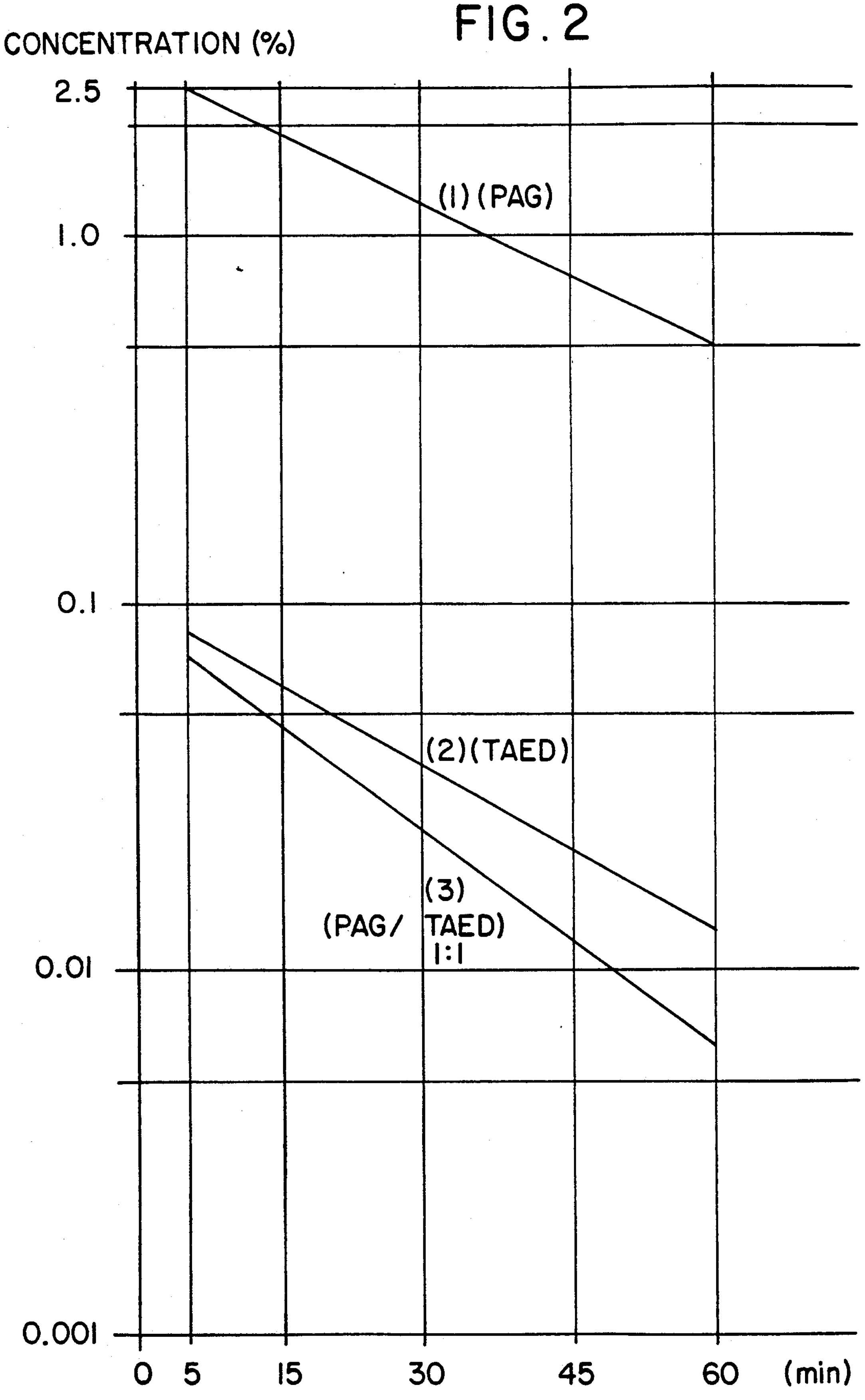
Figure 3:
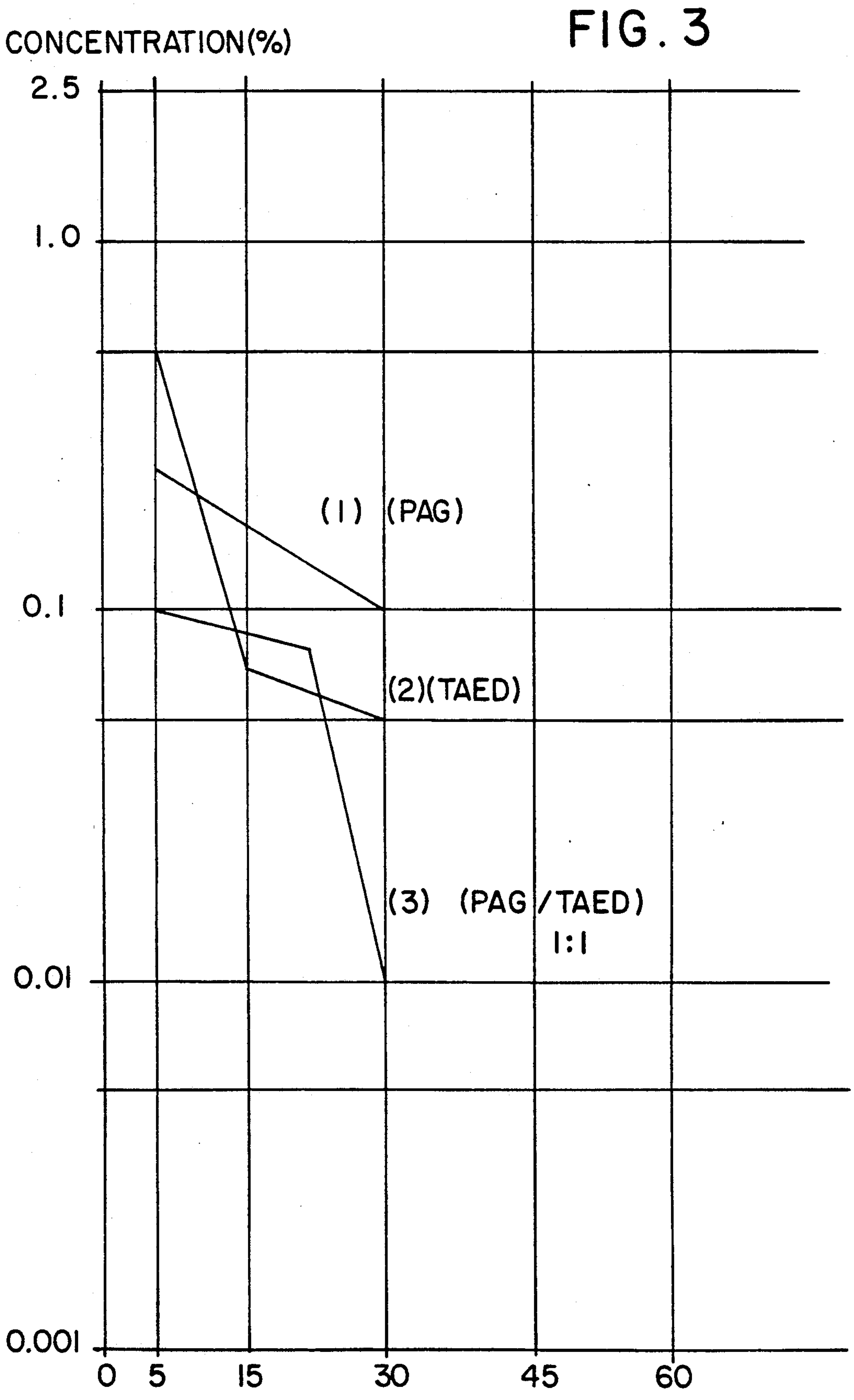

The results obtained during these experiments clearly show the synergistic effect which is obtained when the mixture of TAED and PAG (ratio 1:1) is used according to the invention, in contrast to the results which are obtained with only PAG and TAED. The results obtained during the experiments are illustrated by FIGS. 1-3.

The washing agent produced according to Example 12 was compared with peracetic acid in the test described below, the concentration of the products to be examined was 5 g. per liter (=0.5%).

In the test there were used:

(a) washing agent according to Example 12, (b) per-acetic acid (3.5%, i.e., 0.5% of the 3.5% per-acetic acid corresponds to an application concentration of 0.0175% per-acetic acid), (c) physiological brine as control.

The test procedure consisted in placing a small germ-loaded piece of cloth (of the size 10×10 cm) into the washing agents solution at 40° C. for 15 and 30 minutes respectively.

As inactivation substance to remove residual peroxides and activators, a mixture of 3% Tween 80, 0.5% sodium thiosulphate, 0.1% histidine and 0.3% lecithin were used.

Used test germs:

*Staph. aureus* (ATCC 6538)

*E. coli* (ATCC 8739)

*Candida albicans* (ATCC 10231)

The results obtained during the experiment are set forth in Table II below.

TABLE II

| | Low Temp Washing Agent | | Per-Acetic Acid | | Physiol NaCl Soln | | Control |
|---|---|---|---|---|---|---|---|
| | 15' | 30' | 15' | 30' | 15' | 30' | CFU/ml |
| *Staph. aureus* ATCC 6538 | <10 | <10 | <10 | <10 | $3.6 \times 10^7$ | $2.3 \times 10^8$ | $8.1 \times 10^9$ |
| *E. coli* ATCC 8739 | <10 | <10 | <10 | <10 | $2.2 \times 10^7$ | $3.2 \times 10^8$ | $6.0 \times 10^9$ |
| *Cand. alb* ATCC 10231 | <10 | <10 | <10 | <10 | $3.5 \times 10^4$ | $2.9 \times 10^4$ | $2.3 \times 10^5$ |

These results show that the microbicidal effect of the powdery low-temperature washing agent of the invention corresponds to most of the per-acetic acid. Per-acetic acid may, however, not be used for the purposes of the invention, since it is liquid, has an etching effect, belongs to a group of dangerous working substances, is only stable to a limited extent, is very corrosive and causes problems with the handling (protective gloves, protective glasses, etc).

With the washing agents according to Examples 1-14, instead of sodium tripolyphosphate, a builder such as a zeolite may be used with the same result.

Likewise, instead of sodium metasilicate, sodium disilicate may be also used. Finally, instead of EDTA, the 2 Na-salt of this acid may be used.

I claim:

1. Washing agent comprising surfactants and builders of from 10 to 70% by weight, per-compounds of from 5 to 40% by weight and N,N,N',N'-tetracetylethylene diamine (TAED) as acetyl donor and pentaacetyl glucose (PAG) further donor, wherein the TAED:PAG ratio is 0.75 to 1.25:1.25 to 0.75, total acetyl donors being 2-20% by weight, said weight ratio based on total washing agent, the total weights of said components being 100%.

2. Washing agent according to claim 1, characterized in that N,N,N',N'-tetraacetylethylene diamine and pentaacetyl glucose are provided in a ratio of 0.75 to 1.25:1.25 to 0.75.

3. Washing agent according to claim 1, characterized in that the mixture of the acetyl donors forms 2-20% by weight of the washing agent.

4. Washing agent according to claim 1, characterized in that it comprises as per-compounds, sodium percarbonate, sodium caroate, sodium perborate, sodium percarbamide and/or magnesium monoperoxyphthalate.

5. Washing agent according to claim 4, characterized in that the ratio of the mixture of the acetyl donors to the per-compounds is between 1:1 and 1:3.

6. Washing agent according to claim 1, characterized in that it comprises the following composition:

(a) mixture of tetraacetylethylene diamine and pentaacetyl glucose: 2-20% by weight,
(b) one or more per-compounds: 5-40% by weight,
(c) surfactants and builders: 10-70% by weight,
(d) one or more corrosion inhibitors: 3-15% by weight,
(e) one or more fillers: 8-40% by weight,
(f) greying inhibitors: 0.6-2% by weight,
(g) complex formers: 0.1-2% by weight,
(h) optical brighteners: 0.1-1% by weight,
(i) enzymes, preferably proteolytic enzymes: 0-1.6% by weight,
(j) perfume: 0-2% by weight, as well as as balance, if necessary.

7. Washing agent according to claim 6, characterized by the following composition:

(a) mixture of tetraacetylethylene diamine and pentaacetyl glucose: 4-14% by weight,
(b) one or more per-compounds: 8-25% by weight,
(c) surfactants and builders: 20-60% by weight,
(d) one or more corrosion inhibitors: 5-11% by weight,
(e) one or more fillers: 13-26% by weight,
(f) greying inhibitors: 0.7-2% by weight,
(g) complex formers: 0.2-1% by weight,
(h) optical brighteners: 0.1-0.6% by weight,
(i) enzymes, preferably proteolytic enzymes: 0-1% by weight,
(j) perfume: 0-0.5% by weight, as well as water as balance, if necessary.

8. Washing agent according to claim 7, characterized by the following composition:

(a) mixture of tetraacetylethylene diamine and pentaacetyl glucose in the ratio 1:1: 6-12% by weight,
(b) one or more per-compounds: 10-20% by weight,
(c) surfactants and builders: 35-50% by weight,
(d) one or more corrosion inhibitors: 6-10% by weight,
(e) one or more fillers: 15-22% by weight,
(f) greying inhibitors: 1% by weight,
(g) complex formers: 0.2-0.6% by weight,
(h) enzymes, preferably proteolytic enzymes: 0.5% by weight,
(i) perfume: 0.5% by weight, as well as water as balance, if necessary.

9. A process for the disinfection of bacterially contaminated clothing by washing the same at a temperature at least 40° C. for at least 15 minutes in a washing material comprising surfactants and builders of from 10 to 70% by weight, per-compounds of from 5 to 40% by weight and N,N,N',N'-tetraacetylethylene diamine (TAED) and pentaacetyl glucose (PAG), wherein the TAED:PAG ratio is between 0.75 to 1.25:1.25 to 0.75, the total amount of TAED and PAG comprises between 2 and 20% by weight of the washing agent and the wash solution comprises at least 0.5% by weight of the washing agent.

* * * * *